United States Patent [19]

Fisher et al.

[11] 4,254,095

[45] Mar. 3, 1981

[54] RADIOIMMUNOASSAY FOR ERYTHROPOIETIN

[75] Inventors: James W. Fisher; Arvind B. Rege, both of New Orleans, La.

[73] Assignee: Research Corporation, New York, N.Y.

[21] Appl. No.: 900,580

[22] Filed: Apr. 27, 1978

Related U.S. Application Data

[63] Continuation-in-part of Ser. No. 892,807, Apr. 3, 1978, abandoned.

[51] Int. Cl.³ .................. G01N 33/48; G01T 1/00; C01G 7/00; B65D 7/00
[52] U.S. Cl. ........................... 424/1; 23/230 B; 422/61; 424/12; 424/88
[58] Field of Search .......................... 424/1, 12, 88; 23/230 B; 422/61; 260/112 B

[56] References Cited

PUBLICATIONS

Rege et al., 11, Fed. Proc., 36:1287 (1977).
Fisher et al., Abstract for 3rd Int. Congress of Hematology, Munich, Germany, Aug. 2-8, 1970.
Bolton et al., Biochem. J., 133:529-539 (1973).
Bruno, In New Techniques in Tumor Location and Radioimmonoassay, Ed. Croll et al., J. Wiley and Sons, New York, 1974, pp. 9-15.

*Primary Examiner*—Benjamin R. Padgett
*Assistant Examiner*—Christine M. Nucker
*Attorney, Agent, or Firm*—Sidney B. Williams, Jr.

[57] ABSTRACT

A kit and method for the radioimmunoassay (RIA) for erythropoietin. Also, a method for purifying erythropoietin and purified labelled erythropoietin-conjugate for use as a tracer in the RIA.

53 Claims, 10 Drawing Figures

| Sample Code | A | | B | | C | | D | | E | | F | | G | | H | | I | | J | |
|---|---|---|---|---|---|---|---|---|---|---|---|---|---|---|---|---|---|---|---|---|
| Erythro poietin activity units/ml | BIA | RIA | BIA | RIA | BIA | RIA | BIA | RIA | BIA | RIA | BIA | RIA | BIA | RIA | BIA | RIA | BIA | RIA | BIA | RIA |
| Labs X1 | | | | | | | | | | | | | | | | | | | | |
| X2 | | | | | | | | | | | | | | | | | | | | |
| X3 | | | | | | | | | | | | | | | | | | | | |
| X4 | | | | | | | | | | | | | | | | | | | | |
| X5 | | | | | | | | | | | | | | | | | | | | |
| average Erythro poietin activity u/ml | | | | | | | | | | | | | | | | | | | | |

FIG. 7

RADIOIMMUNOASSAY FOR ERYTHROPOIETIN

The invention described herein was made in the course of, or under U.S.P.H.S. Grant 5R01-AM-13211-08 HEM with the National Institute of Arthritis, Metabolism and Digestive Diseases, National Institutes of Health, Bethesda, Md. 20014.

CROSS REFERENCE TO RELATED APPLICATION

This application is a continuation-in-part of application Ser. No. 892,807, filed Apr. 3, 1978, abandoned.

BACKGROUND OF THE INVENTION

1. Field of the Invention

This invention concerns a radioimmunoassay for erythropoietin. It also concerns a kit containing reagents to be used in said radioimmunoassay.

Erythropoietin is a glycoprotein hormone synthesized in the kidney which acts in the bone marrow to stimulate the production of red blood cells (erythrocytes). Its measurement in human blood is important in the evaluation and differential diagnosis of certain anemias and is also useful in following renal transplant patients. However, the only reliable assay in use today has been a bioassay in which mice are made polycythemic by exposure to hypoxia in special chambers of hypertransfusion and the rate of incorporation of $^{59}Fe$ into newly formed red cells is measured. This assay is not sensitive and practical for routine use and only a small number of research laboratories have developed the bioasay capability.

The earliest in vivo assays for erythropoietin consisted of the measurement of increases in hemoglobin, hematocrit, marrow erythroblasts and blood reticulocytes in normal animals. These techniques were soon replaced by the measurement of $^{59}Fe$ incorporation into newly formed red cells following the administration of plasma to normal rats. See L. T. Plzak et al., J. Lab. Clin. Med. 46:671, 1955. Once the ratio of oxygen supply to oxygen demand was recognized as the controlling signal for erythropoetin production sensitive test animals in which endogenous erythropoietin production has been suppressed by decreasing tissue oxygen demand were used in erythropoietin assays. Various methods of decreasing tissue oxygen demand have been used. For example fasting, see Fried et al., Proc. Soc. Exp. Biol. Med. 94:237 (1957); increasing tissue oxygen supply by the induction of polycychemia with transfusion, see Jacobson L. et al., Proc. Soc. Expl. Biol. Med. 94:243 (1957 and the induction of hypoxia, see Cotes et al., Nature 191:1065-1067 (1967).

In these assays a dose of 0.5 to 1.0 International Reference Preparation (IRP) units of erythropoietin in starved rats and 0.05 to 0.1 units in polycythemic mice were necessary to induce a detectable elevation in the precent $^{59}Fe$ incorporation in newly formed red cells.

Because of the high cost, relative insensitivity and the large amounts of material needed for the in vivo assay for erythropoietin, attempts have been made to develop better in vitro assays for erythropoietin. These methods have included measuring $^{59}Fe$ incorporation heme in marrow cultures, see Krantz et al., J. Biol. Chem. 238:4085 (1963); double immuno diffusion, Krugers et al., Ann: N.Y. Acad. Sci. 149:294 (1968); hemagglutination, Lange et al., J. Lab. Clin. Med. 73:78 (1969), and radioimmunoassay, Fisher et al., "Factors Influencing Renal and Extra Renal Erythropoietin Production", In "Regulation of Erythropoiesis and Haemoglobin Synthesis", (T. Travnicek and Jan Neuwirt eds.), Proceedings of the International Symposium, University Karlova, Praha, 1971, pp. 23-40., Lertora et al., "Studies on Radioimmunoassay for Human Erythropoietin", J. Lab. Clin. Med., 86:140-151 (1975), and Garcia, J. F. "The Radioimmunoassay of Human Plasma Erythropoietin", In Regulation of Erythropoiesis, Gordon A. S. et al., eds., First International conference on Hematopotesis, capri, Italy, 1971, Milano, Italy, 1972, the Publishing House 1 Ponte, pp. 132-153. The marrow culture method has the disadvantage that in order to assay plasmas with low concentrations of erythropoietin, large volumes of plasma must be added to the in vitro medium. Since it contains interfering components the plasma sample becomes the major constituent making it difficult to interpret the results.

Radioimmunoassay has several advantages over the bioassay with regard to sensitivity, specificity, precision and practicality. The basic principle of this procedure is the competition between labelled and unlabelled antigen for a fixed number of antibody binding sites as outlined in FIG. 1. If increasing amounts of unlabelled antigen (i.e. standards or unknowns) and a fixed amount of tracer are allowed to react with a constant and limiting amount of antibody, a decreasing quantity of labelled antigen is bound to the antibody. The bound antigen is separated from free antigen by a suitable technique and percent labelled antigen bound is determined by gamma counting. The relationship of bound labelled antigen to the added non-labelled antigen is expressed as a standard curve and the amount of antigen in the sample is determined by interpolation from this curve. Iodine$^{125}$ is the most widely used isotope to label proteins. It is preferred to $C^{14}$ and tritium because of its high specific activity and ease of labelling and counting. It is better than Iodine$^{131}$ because of its longer half-life. We attempted several iodination techniques to label erythropoietin. These methods included the Chloramine-T method of Greenwood and Hunter (4), the gaseous diffusion method of Butt (5), the microelectrolytic method of Donnabein (6), and the enzymatic iodination method of Marcholonis (7) and David and Reisfeld (8). None of these methods in our hands gave us efficient labelling and the majority of the labelled erythropoietin lost its immunoreactivity after iodination.

The advantages of radioimmunoassay in the identification of erythropoietin have been appreciated, see Fisher et al., I, A Radioimmunoassay for Human Urinary Erythropoietin, Israel Journal of Medical Science, Vol. 7, No. 7-8, pp. 873-876 (July-August, 1971). Fisher et al., II; "Studies on Radioimmunoassay of Human Urinary Erythropoietin", Abstract for 3rd International Congress of Hematology, Munich, Germany, Aug. 28, 1970; Fisher et al., III, "Factors Influencing Renal and Extra Renal Erythropoietin Production", In: Regulation of Erythropoiesis and Hemoglobin Synthesis, T. Travnicek and Jan Newwirt eds., Proceedings of the International Symposium, Universita Karlova, Praha, 1971, pages 23-40, Fisher et al., IV. "A Radioimmunoassay for Human Urinary Erythropoietin", Israel J. Med. Sci., 7:873-876 (1970), Lertora et al., I; "A Radioimmunoassay of Erythropoietin in Serum from Normal and Anemia Uremic Subjects"; Federation Proceedings, 32:872 (1973); Lertora et al., II, "Studies on Radioimmunoassay for Human Erythropoietin", J. Lab. Clin. Med., 86:140-151 (1975).

Fisher et al. I, II, III and Lertora et al., I and II all disclose (1) methods of purifying erythropoietin obtained from the urine of patients with anemia associated with hookworm infestation and (2) radioiodination of Erythropoietin utilizing the Chloramine T labelling method of Greenwood and Hunter. Lertora et al., II, page 149, lines 9 through 11, mention that the use of microelectrolytic procedures, conjugation labelling and enzymatic iodination with lactoperoxidase may reduce the degree of protein damage in the labelling procedure. Except for the conjugation method, using a Bolton-Hunter reagent of the appropriate specific activity, all of the above labelling methods in our hands, have resulted in immunologically inactive labelled erythropoietin or labelled erythropoietin of low activity.

We have labelled purified erythropoietin preparations (8,000–12,000 units/mg protein) with iodine-125 using the Chloramine-T method of Greenwood and Hunter. The majority of the labelled protein obtained by this method was immunologically unreactive, probably as a result of the strong oxidizing property of Chloramine-T.

In order to circumvent the use of strong oxidizing and reducing agents, we iodinated erythropoietin by the microelectrolytic method. This method also resulted in immunologically unreactive labeled erythropoietin. In a search for a better labelling method we have also used the enzymatic lactoperoxidase method for erythropoietin iodination. Since the enzyme lactoperoxidase has a molecular weight of 84,000 and since self-iodination of the enzyme does occur during iodination, separating the enzyme from the labelled erythropoietin is difficult by gel filtration chromatography. The enzyme was therefore coupled to Sepharose 4-B and the coupled enzyme was used to catalyze the iodination reaction. Unreacted iodide was separated from the labelled erythropoietin by fractionation on a Sephadex G-25 column. The pooled protein peak from G-25 was further fractionated on Sephadex G-150. Again two labelled protein peaks were obtained. The minor protein peak appeared in the void volume and had 45–67% maximum binding to the antibody. The major labelled protein peak exhibited about 35% binding. Results obtained using free lactoperoxidase and erythropoietin were not very different from that obtaned with the solid state lactoperoxidase. The lactoperoxidase method was therefore an improvement over the Chloramine-T, and electrolytic methods, however, the labelling efficiency was again only fair and maximum binding was still low.

The Bolton-Hunter method has been used before in an attempt to label erythropoietin, See Rege et al., "Iodination Methods for The Radioimmunoassay of Erythropoietin," 17th Annual Meeting American Soc. Hematology; Atlanta, Ga., Dec. 7 through 10, 1974, p. 78. However, Rege et al. I concluded after experimenting with several methods of labelling erythropoietin that the Chloramine-T method was superior to the others when labelling less than 5 microgram quantities of erythropoietin. Rege et al. II, in 1977, discloses the use of an erythropoietin-conjugate that had been purified by absorption with antiserum to normal human urinary proteins and (2) absorption with anti-erythropoietin antiserum. However this technique fails to yield a tracer suitable for use in a practical and routine RIA.

The difficulty of labelling erythropoietin and, still retaining its biological activity was recognized recently in the development of a procedure for purifying erythropoietin, See Miyake et al., "Purification of Human Erythropoietin," The Journal of Biological Chemistry, Vol. 252:5558 (1977).

It is the primary object of this invention to provide a rapid text and reagents used therein for determining the level of erythropoietin in human sera.

SUMMARY OF THE INVENTION

The above and other objects of the present invention which will become apparent from the following description is obtained with a radioimmunoassay utilizing as a tracer purified labelled erythropoietin. The erythropoietin is labelled utilizing the conjugation labelling method and is purified by immunosorption with antiserum that has been adsorbed with human sera proteins. A preferred embodiment is the purification of the labelled antigen with an antiserum that has been pre-adsorbed with polycythemia vera serum proteins. When ultra-pure erythropoietin is utilized, it is not necessary to further purify the tracer.

The conjugation metod of labelling has proven to be advantageous over other methods because here neither the radionuclid sodium iodide$^{125}$ nor the oxidizing and reducing agents are in contact with the protein to be labelled. In this method as developed by Bolton and Hunter, see Bolton, A. E. and Hunter, W. M., "Labelling of Proteins to High Specific Radioactivity by Conjugation to a $^{125}$I-Containing Acylating Agent", Biochem. J., 133:529–539 (1973), an acylating agent, iodinaed N-succinimidyl ester of 3-(4-hydroxyphenyl)-propionic acid which reacts with the N-terminal amino group or epsilonamino groups of lysine residue is conjugated to the protein. The specific activity of the commercially available iodinated N-succinimidy ester of 3-(4-hydroxyphenyl)-propionic acid is about 1500 curie/millimole.

The RIA of this invention involves
(1) The preparation of purified erythropoietin.
(2) The preparation of labelled erythropoietin conjugate utilizing the Bolton-Hunter method.
(3) Purification of the erythropoietin-conjugate.

BRIEF DESCRIPTION OF DRAWING

FIG. 7 is a form that can be used to record erythropoietin activity and average erythropoietin values in activity units per milliter.

DETAILED DESCRIPTION OF THE INVENTION

(1) Purification of Erythropoietin

Figure 1:
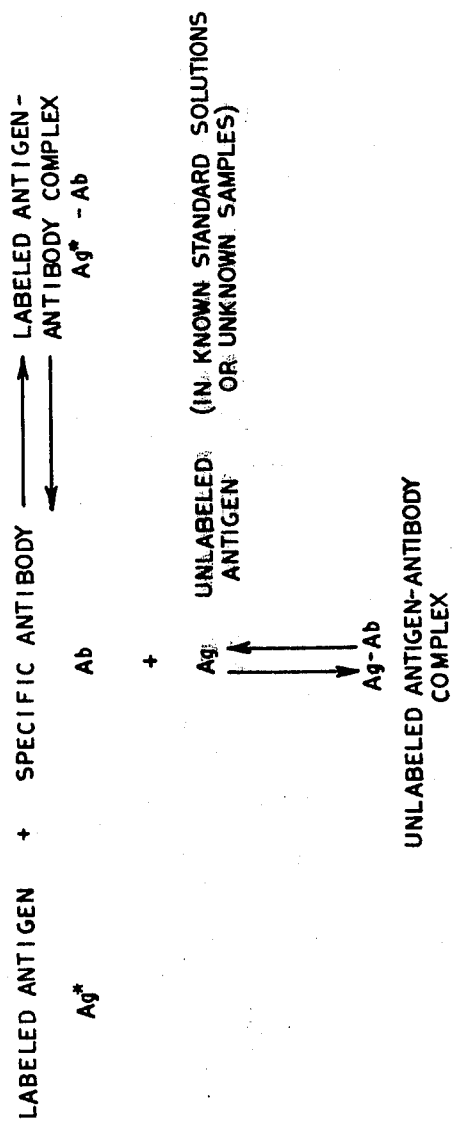
FIG. 1 is a schematic outline of the basic principle of radioimmunoassay.
Figure 2:
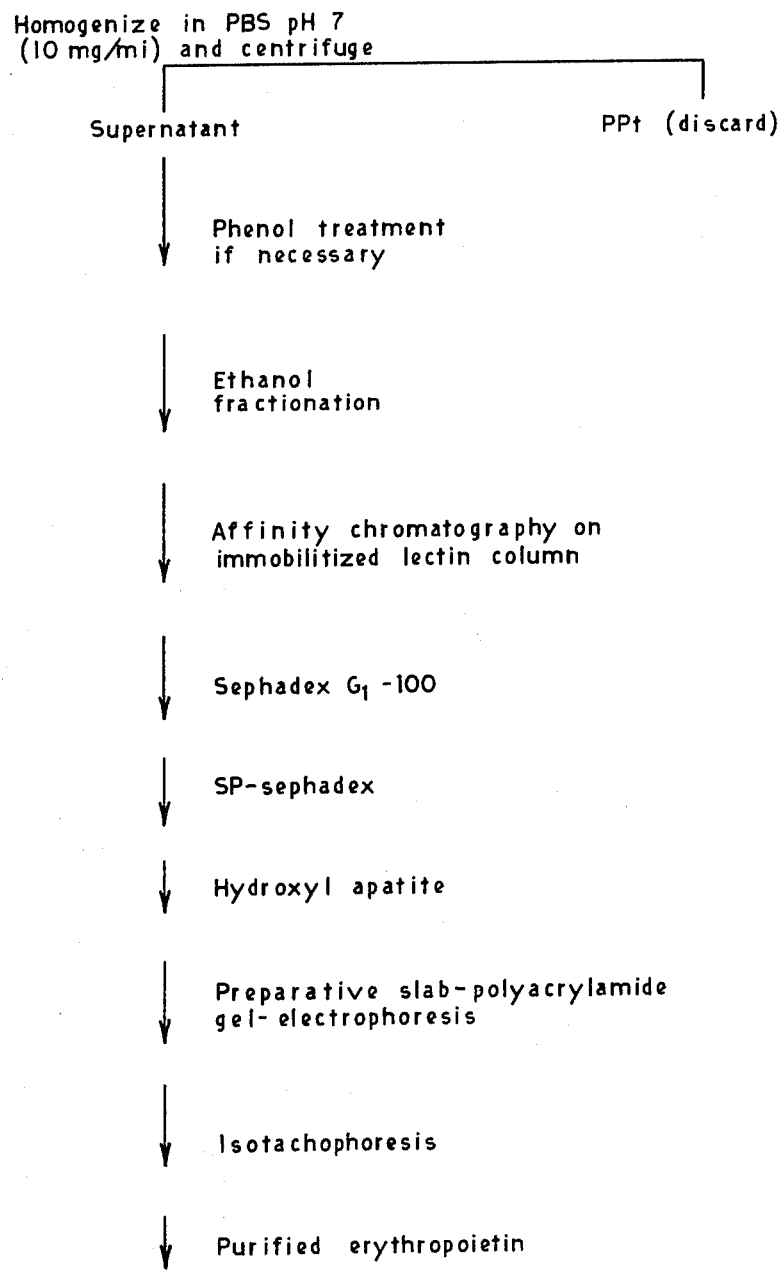
FIG. 2 is a schematic flow chart of a process for purifying urine obtained from patients with hookworm anemia.

The erythropoietin can be obtained from patients suffering from anemia. For example, from the urine of patients with anemia associated with hookworm infestation or aplastic anemia.

Urine rich in erythropoietin from patients with hookworm anemia is purified in accordance with the following scheme 1. Erythropoietic activity at each step assayed by bioassay in exhypoxic polycythemic mouse.
2. Homogenity of the purified erythropoietin confirmed by disc-gel electrophoresis at different PH's, SDS disc-gel electrophoresis and immunoelectrophoresis.

Two purification methods for erythropoietin reported in the literature are:

(1) Espada, J. and Gutinsky A. "Purification De Erythropoietia Urinatia Humana", Acta Physiol. Latinoana, 20:122–129 (1970).

| Results obtained in the steps of the purification process. | | | | |
|---|---|---|---|---|
| Raw Extract[1] | 500.0 | 12 500 | 25.0 | 100.0 |
| Heat treatment | 408.0 | 12 450 | 30.5 | 99.6 |
| 1st DEAE-Cellulose Column | 105.0 | 12 030 | 114.6 | 96.2 |
| Hydroxyl apatite gel | 10.6 | 7 200 | 679.2 | 57.6 |
| 2nd DEAE-Cellulose Column | 8.4 | 7 000 | 833.3 | 56.0 |
| 1st Sephadex G-100 Column | 2.1 | 5 250 | 2 500.0 | 42.0 |
| $2^4$ Sephadex G-100 Column | 0.49 | 3 120 | 6 367.3 | 25.0 |
| $3^3$ Sephadex G-100 Column | 0.29 | 2 345 | 8 086.2 | 16.8 |

[1]Solubilized in phosphate buffer, pH 7.3; 50 mM.

(2) Kawakita M., et al., "Purification of Urinary Erythropoietin", In Erythropoiesis (Nakao, K. et al., eds) pp. 55–64, University of Tokyo Press, Tokyo, Japan (1975).

| Summary of Purification of Erythropoietin. | | | | |
|---|---|---|---|---|
| | | Specific activity | | Activity |
| | Protein (mg) | Mean (IU/mg of protein) | (Maximum) | yield (%) |
| Crude preparation | 1536.3 | 100 | | 100.0 |
| Ca-phosphate gel | 432.5 | 350 | | 98.5 |
| Sephadex G-100 | | | | |
| First No. 49–55* | 25.9 | 2,100 | (3,800) | 71.4 |
| Second (1) No. 51–55[2]* | 6.3 | 4,200 | (11,000) | 34.7 |
| (2) No. 56–59[2]* | 5.5 | 6,300 | (7,800) | 45.5 |
| Third (A) No. 53–55[2]* | 1.2 | 10,000 | (15,000) | 10.2 |
| (B) No. 52–56[2]* | 2.1 | 1,800 | (3,100) | 3.2 |

*The first Sephadex G-100 chromatography was performed 11 times. Total applied protein (Ca-phosphate gel fraction) was 375.8 mg
**Fration Nos. show those in each run and (3) Miyake T. et al., "Purification of Human Erythropoietin", J. Biol. Chem., 252:5558–5564 (1977).

| Purification of Erythropoietin: Summary | | | | | | | |
|---|---|---|---|---|---|---|---|
| | Input | | Product | | Yield (%) | | Mean purification factor |
| | u | Potency u/A | u | Potency u/A | Each Step | overall | |
| DEAE-cellulose | | | 6,976,170 | 89 | 100 | 100 | |
| Phenol | 7,059,670 | 91 | 5,115,110 | 110 | 72 | 72 | 1.21 |
| Ethanol | 5,186,690 | 88 | 4,750,740 | 660 | 92 | 66 | 7.50 |
| DEAE-agarose | 4,566,240 | 563 | 4,052,710 | 1,107 | 89 | 59 | 1.97 |
| Sulfopropyl-Sephadex | 2,480,400 | 1,750 | 1,352,810 | 11,170 | 55 | 32 | 6.38 |
| Sephadex G-100 | 1,259,040 | 12,830 | 1,274,430 | 39,060 | 100 | 32 | 3.04 |
| Hydroxylapatite | 1,083,650 | 38,770 | 721,160 | 82,720 | 67 | 21 | 2.13 |

Ultra pure erythropoietin, such as that obtained by the Miyake et al procedure, can be labelled by the conjugation method and used directly in our radioimmunoassay without subjecting the labelled material to further purification.

Figure 3:
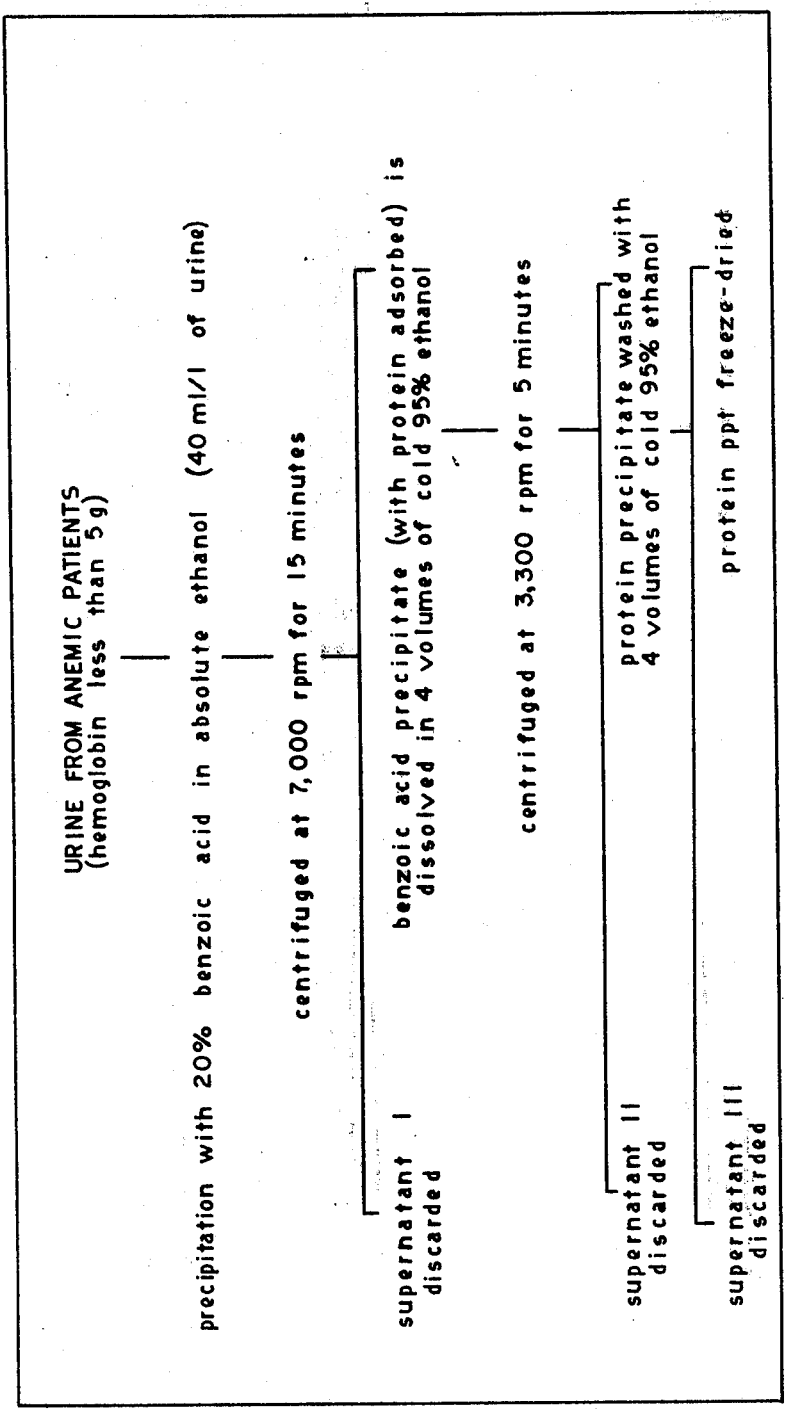
FIG. 3 is a schematic flow chart of a process for concentrating urine obtained from patients with iron deficiency anemia associated with hookworm infestation.

Erythropoietin which has been used in our RIA was concentrated from urine of patients with iron deficiency anemia associated with hookworm infestation, See Espada et al., "A New Method for Concentrating of erythropoietin from human urine", Biochem. Med., 3:475 (1970). The schematic outline of this concentration process is shown in FIG. 3. Erythropoietin concentrated by the benzoic acid method was further purified to specific activity of 8000–10,000 units 1 mg protein by the procedure outlined in the table below.

| PURIFICATION OF HUMAN URINARY ERYTHROPOIETIN | | | |
|---|---|---|---|
| FRACTION | SPECIFIC ACTIVITY (U/mg Protein)* | PURIFICATION FACTOR + | RECOVERY + |
| BENZOIC ACID PRECIPITATE | 192.2 ± 7.8(6) | — | 100 |
| HEAT TREATMENT SEPHADEX G-25 | 385.6 ± 22.9(8) | 2 | 99.2 |
| HYDROXYL APATITE | 2084 ± 175(3) | 10.8 | 54.2 |
| DIALYSIS HYDROXYL APATITE | 1563 ± | 8.1 | 40.7 |
| Fr 7 | 4031 ± 370(4) | 21.0 | 2.4 |
| Fr 8 | 7000 ± 685(4) | 36.4 | 4.2 |
| Fr 9 | 9500 ± 1000(4) | 49.4 | 3.7 |
| Fr 10 | 6778 ± 388(3) | 35.3 | 1.3 |
| Fr 11 | 10000 ± 1296(3) | 52.0 | 1.2 |
| Fr 12 | 7777 ± 1481(3) | 40.5 | 0.9 |

*Mean ± SE. Number of determinations in parenthesis.
+ Relative to benzoic acid precipitate.

(2) The preparation of erythropoietin-conjugate

The purified Erythropoietin is conjugated to the Bolton-Hunter reagent (iodinated [125] succinimidyl ester of 3-(4-hydroxyphenyl)propionic acid).

Figure 4:
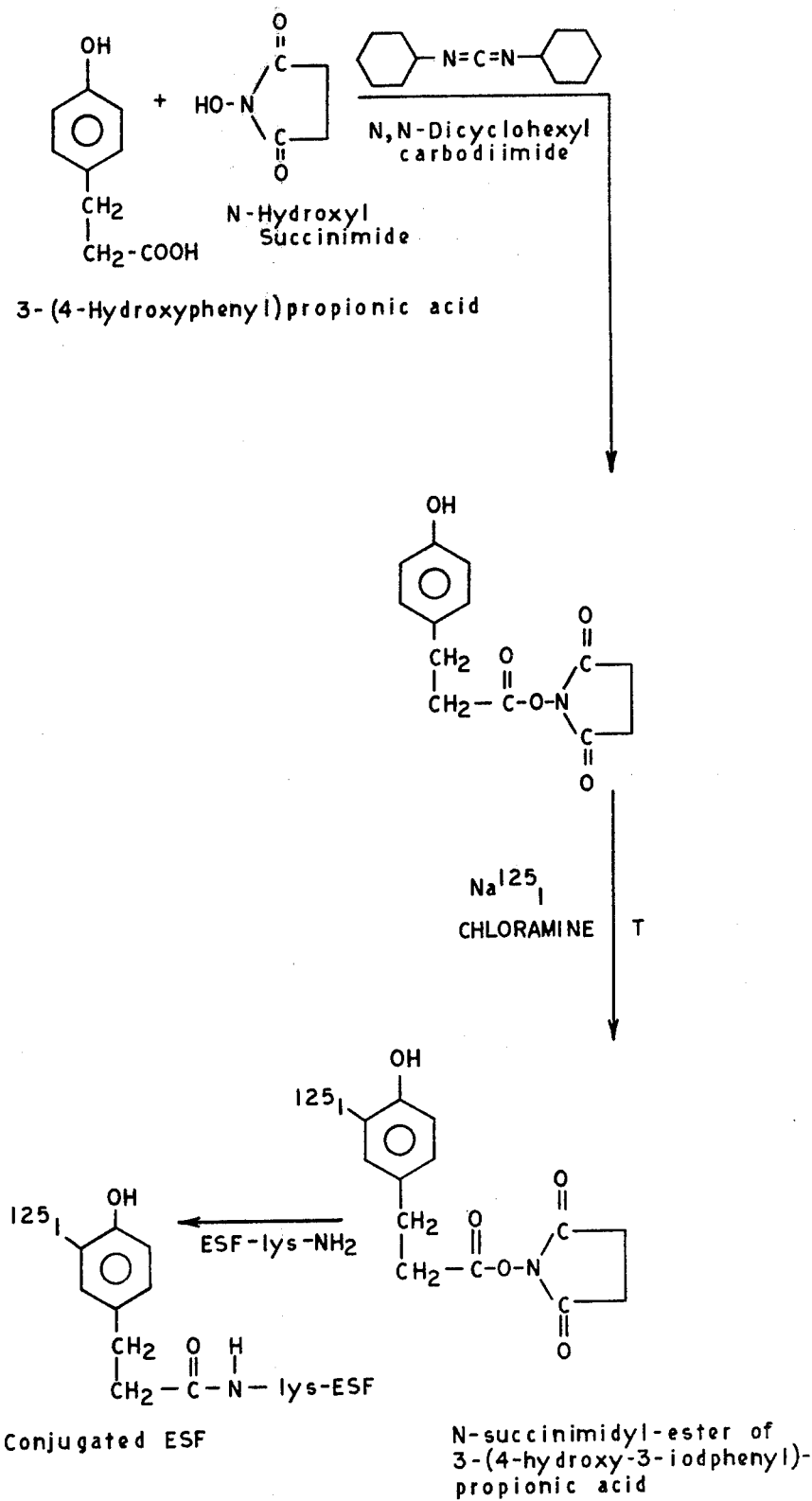
FIG. 4 is a schematic representation of the conjugation labelling of erythropoietin.

The reaction sequence in the conjugation labelling of erythropoietin is illustrated in FIG. 4.

In FIG. 4, ESF is purified erythropoietin, $^{125}I$ is iodine 125 and lys is lysine. The labelling efficiency of this reaction is high and the labelled erythropoietin-conjugate possesses high immunoreactivity. Erythropoietin-conjugate reaction mixture on fractionation on sephadex G-150 gave two protein peaks. A minor protein peak representing erythropoietin nonomer and a major protein peak representing erythropoietin aggregage. The erythropoietin-conjugate monomer is almost devoid of any non-specific binding. However, the erythropoietin-conjugate aggregate has a non-specific binding of 20%.

(3) Purification of the Erythropoietin-conjugate

Figure 5:
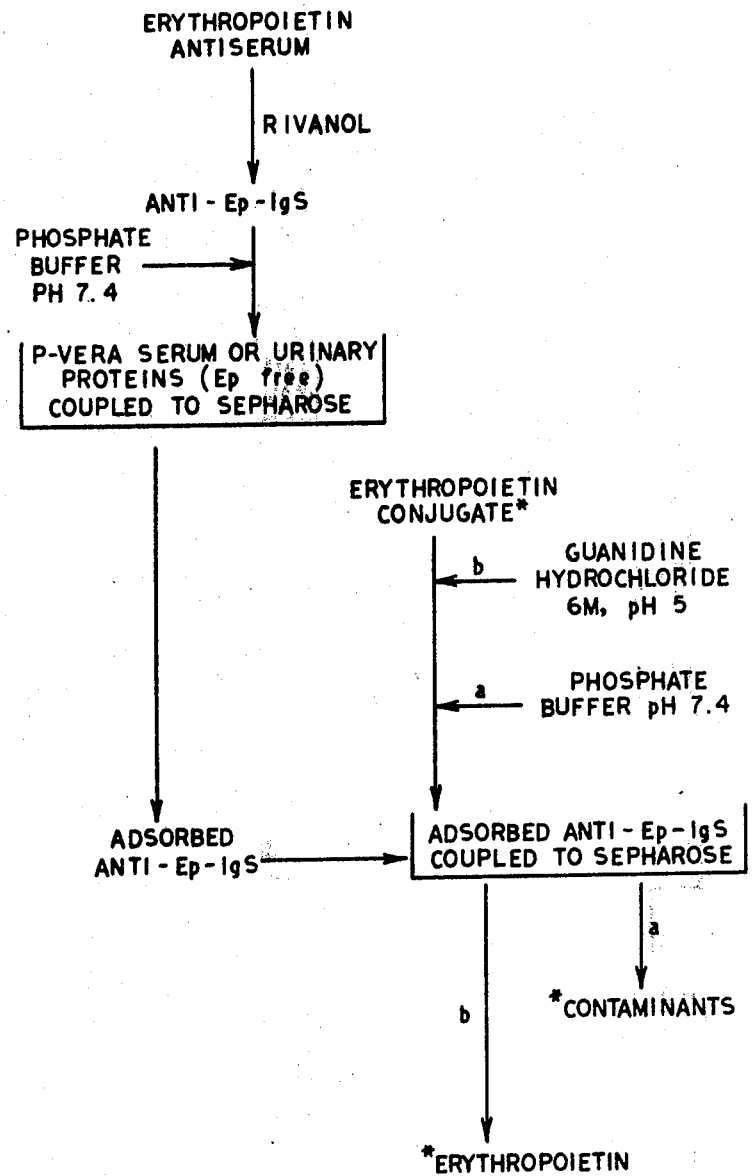
FIG. 5 is a schematic flow chart of a process for purifying erythropoietin antiserum.

The labelled erythropoietin-conjugate is purified by solid-immunosorption techniques using anti-erythropoietin antiserum that was previously adsorbed with human serum proteins. Normal human urinary proteins can be used. However, best results are obtained when the serum used for adsorption is substantially free of erythropoietin. Effective serum includes that obtained from normal humans but which has been treated to remove substantially all of the erythropoietin. Especially effective is polycythemia vera serum. Polycythemia vera serum is devoid of any detectable erythropoietin and removes most of the antibodies other than the anti-erythropoietin antibodies from anti-erythropoietin antiserum. The purification is conducted in accordance to the schematic flow chart shown in FIG. 5.

(1) Serum obtained from a patient with polycythemia vera is coupled to activated Sepharose 4-B and packed in a column.

(2) Anti-erythropoietin antiserum is now eluted from this column. One ml fractions are collected and monitored for protein concentration by measuring O.D. at 280 nm. Fractions under the protein peak are pooled and tested in the polycythemic mouse assay for anti-erythropoietin activity and by Ouchterlongy gel diffusion for the absence of precipitating antibodies against human serum proteins from patients with polycythemia vera. A preferred method of conducting this step involves utilizing anti-erythropoietin immunoglobulins prepared by the Rivanol method. See Abraham E. E. and Odell W. D. in "Immunologic Methods in Steroid Determinations", Persons, F. G. and Caldwell B. U., ed., Appleton-Century-Crops, N.Y., 1970, p. 87. The Rivanol method involves mixing about one (1) part by volume of erythropoietin antiserum with about four (4) parts by volume of an 0.4 percent aqueous solution of Rivanol (2-ethoxy-6,9-diaminoacridine lactate) and allowing the mixture to stand at room temperature for about fifteen (15) minutes. The mixture is then centrifuged and the supernatant, which contains the purified anti-erythropoietin immunoglobulins, is decanted. The supernatant is then treated with carbon black and centrifuged to yield purified anti-erythropoietin immunoglobulins. The IgA fraction of erythropoietin antiserum prepared on DEHE Sephadex (dextran 2-(diethylamino)ethyl 2-[[2-(diethylamino)ethyl]-diethylammonio]ethyl-ether chloride hydrochloride epichlorohydrin crosslinked) can also be used as antiserum.

(3) The adsorbed antiserum so obtained is coupled to Sepharose 4-B and packed in a column.

(4) The labelled erythropoietin is then passed through the column. One ml fractions are collected and monitored for 125-I labelled protein by counting on a Gamma Counter.

(5) The column is washed with 0.02 M phosphate buffer at pH 7.5 until the eluate is free of any labelled protein.

(6) The antigen-antibody complex is then dissociated by and the labelled erythropoietin eluted from the column with 6 M guanidine hydrochloride at pH 5. Fractions under the labelled erythropoietin peak are pooled together and dialyzed against 0.02 M pO4 buffer pH at 7.5.

Purification of the erythropoietin-conjugate utilizing this method can improve its specific binding by an additional 15 to 20%. The erythropoietin conjugate mixture fed to the SEPHAROSE 4-B column contains 90% of the contaminants and only 10% of the desired erythropoietin conjugate. Effectiveness of the purification scheme is confirmed by the fact that purified erythropoietin has increased immunoreactivity whereas the contaminants are practically devoid of any immunoreactivity with adsorbed antiserum as the binder.

(4) Stability of the Erythropoietin-Conjugate Tracer

A standard erythropoietin dose-response curve is obtained once a week for a period of 8 weeks using the same tracer, antibody, standards, buffers and any other reagents and the stability of the labelled preparation is judged by any change in percent binding from the values obtained initially, a shift in the standard curve or an increase in the RIA blank.

The following preparations and examples are illustrative of the assay, reagents and processes of the present invention but are not to be construed as limiting.

In this regard the assay can be used to determine erythropoietin levels in mammals, other than humans, by modifications that would be obvious to those skilled in the art.

Preparation 1

Purification of Erythropoietin

The following quantities are used for processing one liter of urine. The urine is adjusted to pH 6.5 using an acetic acid or sodium hydroxide. It is stirred vigorously and 40 ml of ethanolic solution of benzoic acid (20%) is added rapidly. All operations unless otherwise mentioned are carried out at 4° C. The precipitate of benzoic acid is stirred for 5 minutes and centrifuged at 9000 g for 20 minutes. With large quantities of urine, the benzoic acid suspension is allowed to settle for 3 hours, the supernatant is siphoned off and the precipitate is collected by centrifugation.

The benzoic acid precipitate is dissolved in 60 ml of tris-ethanol solution at −10° C., stirred until completely dissolved, allowed to stand at −10° C. for 1 hour and then centrifuged at 2000 g for 5 minutes. The supernatant is discarded and the pellet is resuspended in 20 ml of cold absolute ethanol at −10° C. The solid material is separated by centrifugation, dried in a desiccator and pulverized. This concentrate which contains 0.5 mg protein per mg is suspended in ice cold water (8 mg/ml) in a Potter-Elvehjem homogenizer with a loosely fitting Teflon pestle to insure complete wetting. The suspension is heated in a boiling water bath for 45 seconds (maximum temperature reached in the suspension is 60°

C.). The rechilled suspension is centrifuged and the supernatant is put aside. The pellet is re-extracted twice more with water without the heat step. The supernatants are pooled, lyophilized, redissolved in a small volume of water and chromatographed at 4° C. on a Sephadex G-25 gel Pharmacia column with water as the developing solvent. All the protein with erythropoietin activity appears in the excluded volume, whereas most of the salts and pigments, and some protein are retained on the column. The erythropoietin containing protein solution is lyophilized. This preparation contains 0.825 mg protein per mg.

The next purification steps involve chromatography on Hydroxyl apatite gel (Biorad) at 4° C. The dimmensions of the gel in the column are 0.9×6.6 cm. A linear gradient of eluting buffer from $10^{-4}$ M to $10^{-2}$ M sodium phosphate at pH 7.0, provided by an ISCO DIAL-GRAD programmable pump system, was employed. The eluate emerging from the column is concentrated 5-7 fold by an Amico CEC ultrafiltration device, equipped with DM-10 membrane, which retains all erythropoietin activity. The total rate of flow (concentrate+ultrafiltrate) is adjusted to about 5 ml/hours. 31.1 mg of preparation H-14-TalSL are dissolved in 31.1 ml buffer at the starting concentration and applied to the column, then the elution program is initiated. Fractions consisting of 1.8 ml concentrate are collected. Fraction T5-11 (conductivity: 198 μmho, pH: 7.3) contains a large proportion of the applied erythropoietin at a much improved specific acitivity. This fraction is dialyzed over a 24 hour period against 3 changes of 200 volumes of buffer of the starting concentration. The resulting 6 ml dialyzard with a conductivity of 48 μmho are rechromatographed on Hydroxyl apatite gel. Fractions collected are stored in a liquid nitrogen freezer.

Absorbance at 280 nm and protein content by the method of Lowry et al. with bovine serum albumin as a standard are determined for the solutions of erythropoietin obtained in the purification scheme. The biological potency of erythropoietin preparation is estimated by the exhypoxic polycythemic mouse assay (Cotes, P. M. and Bangham, D. R.: Bioassay of erythropoietin in mice made polycythaemic by exposure to air at reduced pressure. Nature 191:1065-1067, 1961).

Preparation 2

Erythropoietin Free Sera

Anti-erythropoietin immunoglobulins prepared from anti-erythropoietin antiserum by the Rivanol method are coupled to activated Sepharose 4-B, packed in a column and serum to be made erythropoietin free is recycled through and then eluted with phosphate buffer. One ml fractions are collected and monitored for protein by measuring absorbance at 280 nm.

Preparation 2a

Ertyhropoietin Free Urine

Anti-erythropoietin immunoglobulins prepared from anti-erythropoietin antiserum by the Rivanol method are coupled to activated Sepharose 4-B, packed in a column and urinary proteins to be made erythropoietin free are recycled and eluted through with phosphate buffer. One ml fractions are collected and monitored for protein by measuring absorbance at 280 nm.

Example 1

Erythropoietin-Conjugate

Nine micrograms of a human urinary erythropoietin (9,000/units mg protein) purified in accordance with Preparation 1 is reacted with one millicurie of iodinated N-succinimidyl ester of 3-(4-hydroxyphenyl)propionic acid (Bolton-Hunter Reagent) in 0.1 M borate buffer at a pH 8.5 in an ice bath for 60 minutes. Excess reagent is inactivated with 0.2 M glycine in 0.1 M borate buffer and the reaction mixture is fractionated on a Sephadex G-150 column which was previously saturated and equilibrated with 0.02 M $PO_4$ buffer pH 7.5 with 0.25 gelatin.

Figure 6:
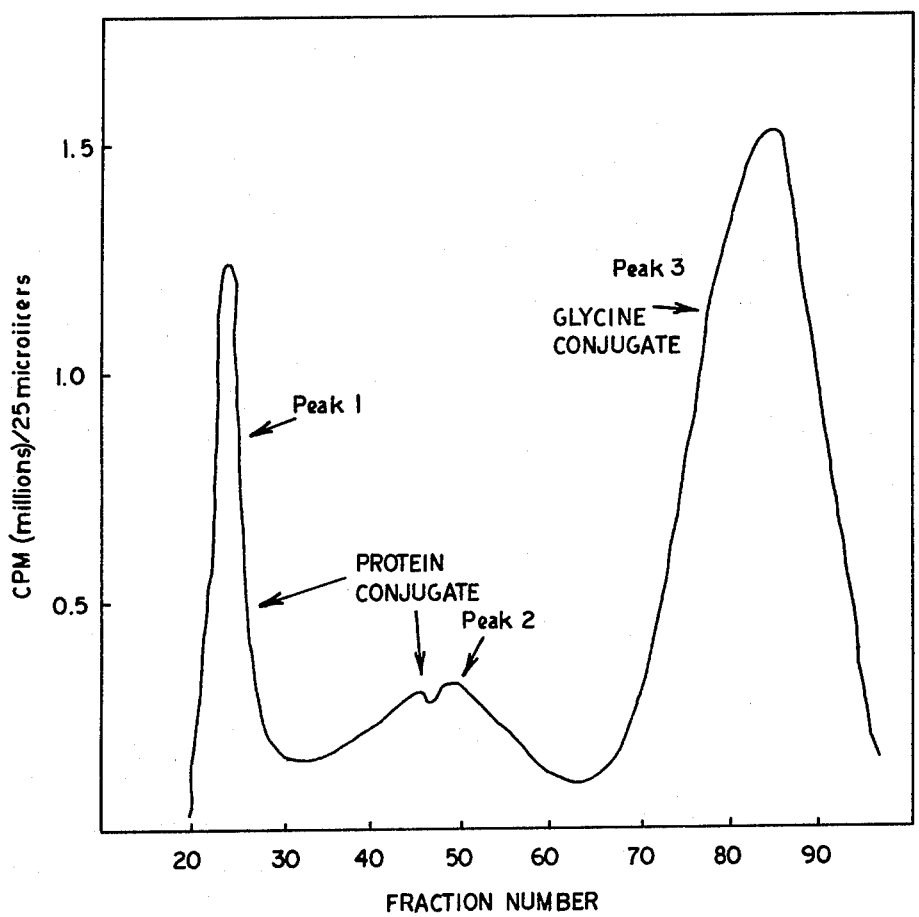
FIG. 6 is a graph showing the fractionation patterns of an erythropoietin conjugte when fractionated on a Sephadex G-150 column.

FIG. 6 shows the fractionation pattern. On the ordinate is CPM (millions)/25 lambda and on the abscissa the fraction number. Two protein peaks are obtained. The majority of the labelled protein appears in the void volume indicating that it is an aggregate of erythropoietin. Peak 1 shows a maximum binding of 75% and a non-specific binding of 20%. Peak 2 shows a maximum binding of 75% but a non specic binding of only 1.7%. Specific activity of the labelled protein is 55μ Ci/μgm protein.

Proteins under both peaks show less maximum binding with antiserum adsorbed with human urinary proteins or polycythemia vera serum and show abnormally high values of erythropoietin in normal human serum samples. This suggests the presence of contaminating proteins in the labelled erythropoietin.

Purification of the labelled erythropoietin can be carried out using the procedure of Examples 2 and 3.

Example 2

Purification of Labelled Erythropoietin Using Erythropoietin Antiserum that has Been Absorbed With Human Urinary Proteins From Patients With Polycythemia Vera and Made Erythropoietin Free The urinary protein preparation from patient with polycythemia vera is made erythropoietin free by adsorption with anti-erythropoietin immunoglobulins. Adsorbed urinary proteins are then coupled to Sepharose 4-B, packed in a column and anti-erythropoietin immunoglobulins are eluted through. One ml. fractions are collected and monitored for proteins concentration by measuring optical density at 280 mn. Fractions under the protein peak are pooled and tested in the polycythemic mouse assay for anti-erythropoietin activity and by *Ouchterlongy gel diffusion* for the absence of precipitating antibodies against erythropoietin free human urinary proteins.

The adsorbed antiserum so obtained is coupled to Sepharose 4-B and packed in a column and the labelled erythropoietin peak (fraction 21 to 28 obtained in Preparation 1) is eluted through the column with phosphate buffer. One ml fractions are collected and monitored for labelled protein by counting on a Gamma Counter. The column is washed with 0.02 phosphate buffer at pH 7.5 until the eluate is free of any labelled protein. The labelled erythropoietin antibody complex is dissociated by and the labelled erythropoietin eluted from the column with 6 M quanidine hydrochloride at pH 5. Fractions under the labelled erythropoietin peak are pooled together and dialyzed against 0.02 M phosphate buffer pH 7.5 to yield 10% of purified labelled erythropoietin.

Example 3

Purification of Labelled Erythropoietin With Anti-Erythropoietin Immunoglobulins that have Been Adsorbed With Human Serum Proteins From Patients With Polycythemia Vera or that were made Erythropoietin Free.

Human serum protein preparation obtained from sera of patients with polycythemia vera is made erythropoietin free by adsorbing with anti-erythropoietin immunoglobulins. Adsorbed serum proteins are then coupled to activated Sepharose 4-B and packed in a column. Anti-erythropoietin immunoglobulin preparation is eluted through the column and one ml fractions are collected and monitored for protein concentration by measuring optical density at 280 mm. Fractions under the protein peak are pooled and tested in the polycythemic mouse assay for anti-erythropoietin activity and by Ouchterlony gel diffusion for the absence of precipitating antibodies against erythropoietin free human serum proteins.

The adsorbed antiserum so obtained is coupled to Sepharose 4-B and packed in a column and the labelled erythropoietin peak (fraction 21 to 28 obtained in Preparation 1) is eluted through the column. One ml fractions are collected and monitored for labelled protein by counting on a Gamma Counter. The column is washed with 0.02 phosphate buffer at pH 7.5 until the eluate is free of any labelled protein. The labelled erythropoietin antibody complex is dissociated by and labelled erythropoietin eluted from the column with 6 M guanidine hydrochloride at pH 5. Fractions under the labelled erythropoietin peak are pooled together and dialyzed against 0.02 M phosphate buffer pH 7.5 to yield 10% of purified labelled erythropoietin having a specific activity of 55 microcurie/and an increase in immunoreactivity of 15 to 20% over that of the unpurified labelled erythropoietin.

Example 3

RIA Kit for Serum Erythropoietin Activity (A) Applicants' RIA kit for erythropoietin is designed so that it provides
1. A container
2. Small containers having all necessary reagents therein.
3. A simple and convenient protocol
4. Quality control for the performance of the entire system
5. A clinically evaluated procedure
6. A rapid and sensitive assay
7. Complete quantitation
8. Minimum non-specific protein effect
9. Efficient separation of bound from free tracer
10. A stable assay system with reproducible results
11. Results which correlate very well with the bioassay for erythropoietin hormone The larger container which holds the smaller containers can be made of styrofoam or any other material which is reasonably impact resistant. The styrofoam or other material is solid throughout with holes in the top wherein the smaller containers, usually circular vials, will snugly fit. Inside the smaller containers will be the reagents used in the radioimmunoassay. The larger container may also contain a packet or other means for holding the protocol and other instructions for use of the smaller container.

(B) Reagents

All necessary reagents are supplied with the kit and are prepared so that they can be shipped at ambient temperature in a stable form and maybe stored upon receipt at the usual refrigerator temperature (2°–8° C.).

Methods for preparing the reagents so that they remain stable at room temperature are well known in the art. After initial reconstitution, the reagents are stable for the useful life of the kit if the specific storage precautions given below are followed. Sodium azide and inhibitors of proteolytic enzymes will be used where appropriate.

Lyophilized assay buffer concentrate (Diluent)

A freeze dried phosphate buffer is supplied. It should be diluted to the specified quantity with distilled water. The resulting assay buffer will be 0.02 M phosphate buffer at pH 7.4±0.2 with 0.1% BSA (Bovine serum albumin).

Lyophilized rabbit serum control diluent (SCD)

A freeze dried rabbit serum control diluent is supplied. For use it will be diluted with distilled water to the specified quantity. The resulting solution will be 0.02 M phosphate buffer at pH 7.4±0.2 with 0.1% BSA and 1% commercial normal rabbit serum.

Lyophilized anti-erythropoietin antiserum (rabbit)

The antiserum is prepared in rabbits against purified human urinary erythropoietin. It is supplied concentrated in a lyophilized form. Each vial is to be reconstituted in the specified quantity of serum control diluent (SCD). In the final solution, the antiserum is sufficient to bind above 40% of the labelled erythropoietin in the absence of unlabelled erythropoietin when used as directed in this procedure, 0.1 ml per tube. It should be stored frozen after reconstitution, preferably in amounts sufficient for a single run. The reconstituted antiserum is stable if stored properly. Deterioration is indicated by a sharp drop in binding from previous levels or a decrease in sensitivity of the standard curve.

Goat anti-rabbit γ-globulin (GARGG)

It is supplied freeze dried. For use it should be diluted to a specified quantity with the diluent and stored frozen after reconstitution, preferably in amounts sufficient for a single run.

Erythropoietin Bolton-Hunter conjugate ($^{125}$I)

(Approximately 1.13 μCi per vial on calibration date)

The labelled erythropoietin is supplied as a lyophilized concentrated solution in 0.02 M phosphate bufferm pH 7.4±0.02 with 0.1% BSA. It is a monoiodinated Bolton-Hunter reagent-erythropoietin-conjugate with a specific activity of >50 μCi/μg. For use it is to be diluted to a specified quantity with the diluent. Use of 0.05 ml of the diluted tracer per tube should provide approximately 10,000 cpm at 50% counting efficiency on the calibration date. Store at −20° C. after dilution. The labelled antigen should be stable when stored in this manner and the extent of its usefulness will usually be dictated only by the half life of iodine $^{125}$. Indications of its deterioration would be a significant decrease in binding from previous levels, a shift in the standard curve or an increase in the RIA blank.

Erythropoietin standards

Six vials of lyophilized standards of Human Urinary Erythropoietin from patients with iron deficiency anemia associated with hookworm disease are supplied. Reconstitute each with the diluent to the specified volume. Upon reconstituting, the resulting solutions will contain 2.5, 5, 10, 20, 40 and 80 mu/ml of erythropoietin. Use 0.05 ml per tube. Store frozen after reconstitution and mix well before use. The standards are stable if stored at −20° C. Deterioration is indicated by a decrease in sensitivity of the standard curve.

All of the reagents can be lyophilized by methods well known in the art.

(C) Radioimmunoassay protocol

| Protocol All volumes are expressed in microliters (ul) | | | | | | |
|---|---|---|---|---|---|---|
| Time | Di- luent | Serum Control Diluent | Anti- serum | Stan- dard | Sam- ple | Tracer |
| 1,2 control | 150 | 100 | -- | -- | -- | 50 |
| 3,4 '0' standard | 150 | -- | 100 | -- | -- | 50 |
| 5-16 standards | 100 | -- | 100 | 50 | -- | 50 |
| 17,18 sample | 100 | -- | 100 | -- | 50 | 50 |

*If the 50 microliter sample does not provide a value on the readable portion of the standard curve use 50 microliters of the appropriate dilutions of the sample; dilutions being made with the diluent. To avoid repetition of the experiment two tubes each may be used for 1:2 and 1:4 sample dilutions along with two tubes for each undiluted sample.

Allow the tubes to incubate at 4° C. for 72 hours. Add 100 microliters of goat anti-rabbit γ-glubulin (GARGG) to each tube and continue incubation at 4° C. for an additional 16 hours (minimum). Add 300 microliters of diluent to each tube and count the tubes in a gamma counter for total radioactivity in each tube. Centrifuge the tubes in a refrigerated centrifuge at 6500 rpm for 30 minutes. Aspirate the supernatent and count the tubes in a gamma counter to determine the percent of the label which is bound.

(D) Calculations

1. Convert the count rate for each tube to counts per minute.

2. Determine the average counts per minute for each set of duplicates.

3. Calculate average net counts per minute for samples and standards (total and bound) by subtracting from each average control counts per minute.

4.

$$\% \text{ bound} = \frac{\text{average net bound CPM}}{\text{average net total CPM}} \times 100$$

5. Using a semilogarithmic graph paper plot the % bound for each standard against the erythropoietin concentration of that standard expressed as mu/ml.

6. Determine the amount of erythropoietin in mu/ml for each serum sample assayed by interpolation from the standard curve.

(E) Correlation with bioassay (polycythemic mouse assay)

Figure 8:
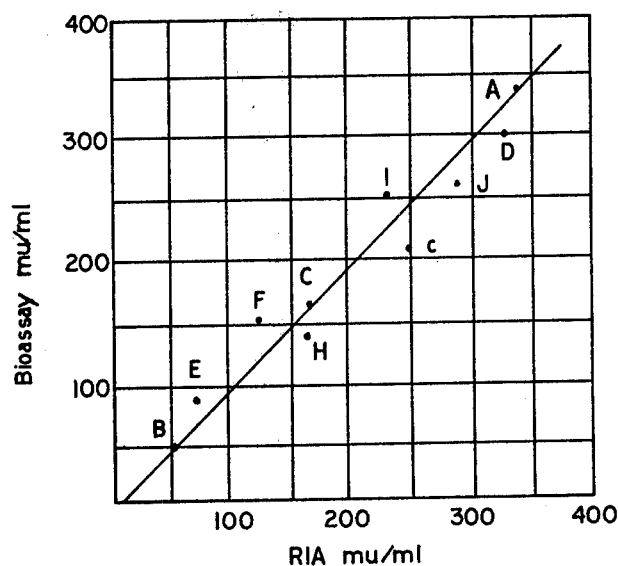
FIG. 8 is a graph showing the correlation of bioassay and radioimmunoassay.

Erythropoietin coded samples with erythropoietic activity ranging from 100 to 400 mu/ml are prepared and coded as unknowns. The erythropoietic activity in the coded samples by bioassay (exhypoxic polycythemic mouse assay) and by radioimmunoassay using the RIA kit is determined. The average erythropoietin activity for each coded sample as determined by bioassay and RIA is then calculated and correlated as shown below. The form used in FIG. 7 can be used to record erythropoietin activity and average erythropoietin activity. The correlation of average erythropoietin activity determined by bioassay and radioimmunoassay is shown in FIG. 8.

Using the purified labelled erythropoietin prepared as outlined in Preparation 2 (using serum proteins from patients with polycythemia vera to adsorb anti-erythropoietin immunoglobulins) together with the other reagents described above and following the protocal outlined above the serum erythropoietin levels of 6 normal human subjects were determined.

Figure 9:
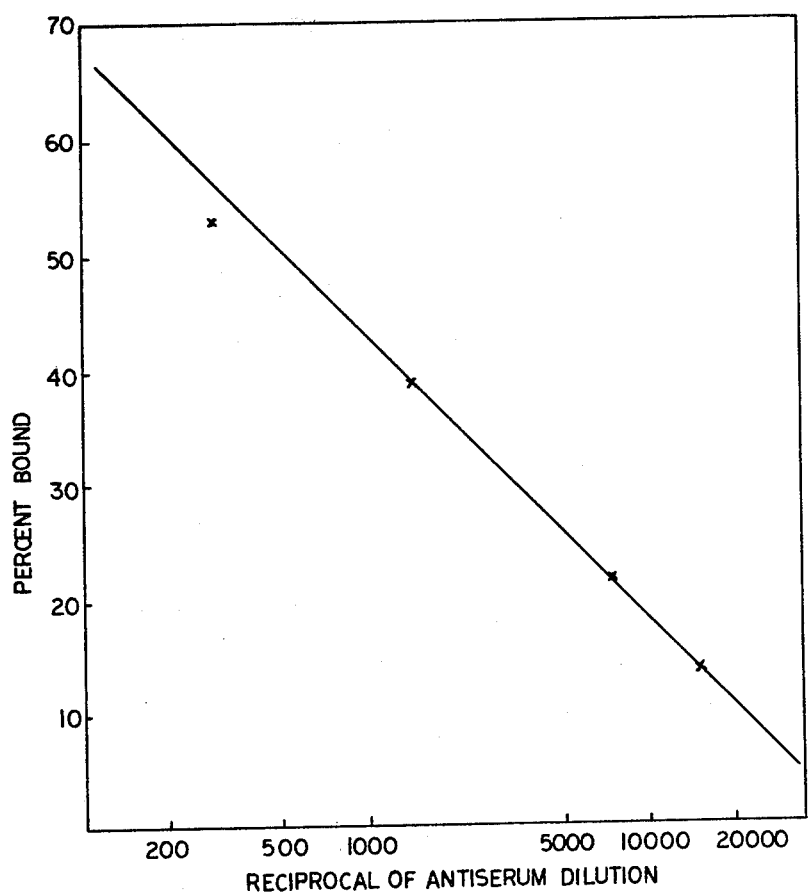
FIG. 9 shows the erythropoietin antiserum dilution curve.
Figure 10:
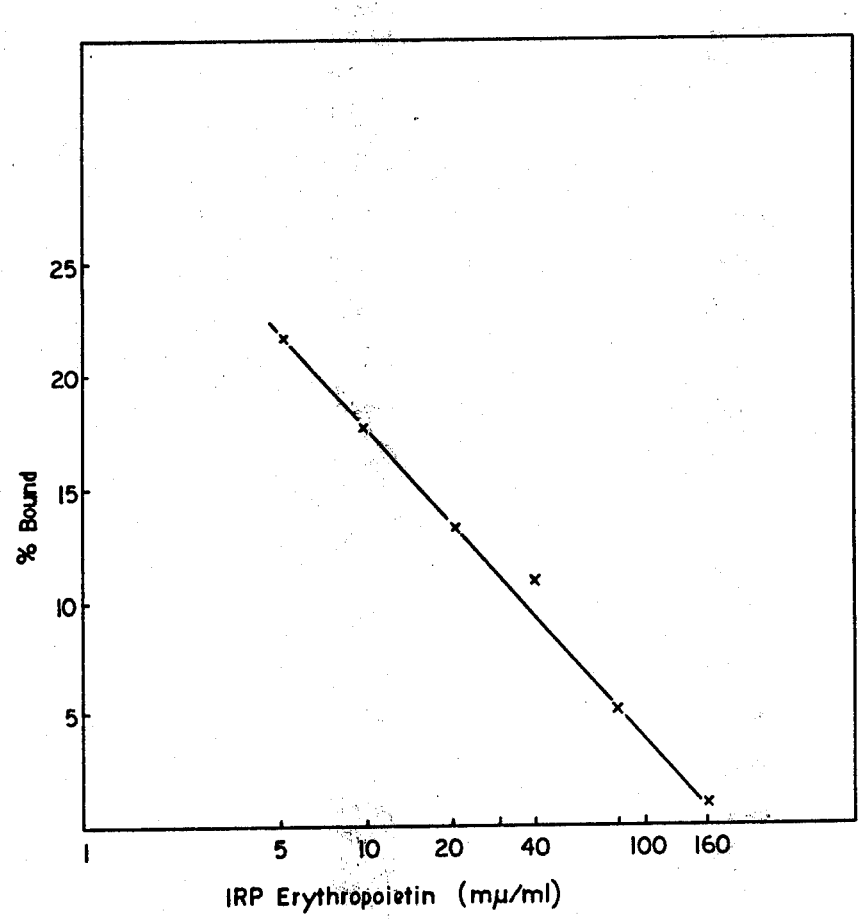
FIG. 10 shows the standard IRP dose-response regression line obtained using purified labelled erythropoietin and erythropoietin antiserum (1:1200 dilution).

FIG. 9 shows the antiserum dilution curve and FIG. 10 shows the International Reference Preparation (IRP) dose response regression line. The dose response curve is linear over the concentration of IRP tested in the assay namely from 5 to 160 mu/ml of erythropoietin. From this standard dose-response regression line, the normal serum erythropoietin levels are found to be in the range of 28 to 50 mu/ml with a mean of 40.16±11.84 mu/ml.

| NORMAL HUMAN SERUM ERYTHROPOIETIN TITERS | | |
|---|---|---|
| SUBJECT | ERYTHROPOIETIN mu/ml | MEAN ± S.D. (SEM) |
| Y.O. | 24 | |
| C.B. | 42 | |
| Ra.S. | 30 | 40.16 ± 11.84 (4.83) |
| E.S. | 39 | |
| F.P. | 54 | |
| R.S. | 52 | |

We claim:

1. In a radioimmunoassay of erythropoietin comprising
    (a) reacting binder containing a fixed number of antibody binding sites with a mixture of labelled and unlabelled erythropoietin;
    (b) separating bound erythropoietin from free erythropoietin; and
    (c) determining the percent labelled erythropoietin bound; the improvement comprising the use of labelled erythropoietin prepared by the conjugation labelling technique wherein the labelled erythropoietin has been purified by immunosorption with anti-erythropoietin antiserum that has been preadsorbed with human proteins that are low in erythropoietin content.

2. A radioimmunoassay in accordance with claim 1 wherein the human proteins are selected from the group consisting of human serum proteins and human urinary proteins.

3. A radioimmunoassay according to claim 2 wherein the human proteins are human serum proteins.

4. A radioimmunoassay according to claim 3 wherein the human serum proteins are substantially free of erythropoietin.

5. A radioimmunoassay according to claim 4 wherein the human serum protein is polycythemia vera serum protein.

6. A radioimmunoassay in accordance with claim 1 wherein the erythropoietin antiserum used is selected from whole erythropoietin antiserum and antierythropoietin immunoglobulins.

7. A radioimmunoassay according to claim 6 wherein the human protein is human urinary protein.

8. A radioimmunoassay in accordance with claim 7 wherein the erythropoietin antiserum is antierythropoietin immunoglobulin.

9. A radioimmunoassay in accordance with claim 8 wherein the erythropoietin antiserum is the immunoglobulin fraction prepared by Rivanol precipitation.

10. A radioimmunoassay in accordance with claim 8 wherein the erythropoietin antiserum is the IgA fraction prepared by fractionation on dextran 2-(diethylamino)ethyl 2[[-(diethylamino)-ethyl]-diethylammonio]ethyl ether chloride hydrochloride epichlorohydrin cross-linked.

11. A radioimmunoassay in accordance with claim 5 wherein the erythropoietin antiserum used is selected from whole erythropoietin antiserum and antierythropoietin immunoglobulins.

12. A radioimmunoassay in accordance with claim 11 wherein the erythropoietin antiserum is antierythropoietin immunoglobulins.

13. A radioimmunoassay in accordance with claim 12 wherein the erythropoietin antiserum is the immunoglobulin fraction prepared by Rivanol precipitation.

14. A radioimmunoassay in accordance with claim 12 wherein the erythropoietin antiserum is the IgA fraction prepared by fractionation on DEAE sephadex.

15. A radioimmunoassay in accordance with claim 1 wherein the erythropoietin conjugate is lyophillized.

16. A radioimmunoassay in accordance with claim 5 wherein the erythropoietin conjugate is lyophillized.

17. A radioimmunoassay in accordance with claim 12 wherein the erythropoietin conjugate is lyophillized.

18. An erythropoietin-conjugate having the structure.

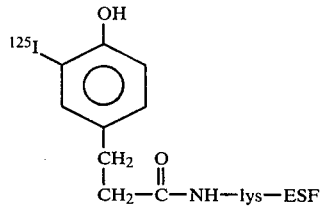

wherein ESF is erythropoietin, lys is lysine and $^{125}I$ is iodine-125, being substantially free of urinary proteins, having a specific activity of between 40 and 55 microcuri/microgram and an immunoreactivity of between 75 and 90 percent.

19. An antigen-antibody complex comprising
(1) purified erythropoietin that has been conjugated with $^{125}$Iodinated p-hydroxyphenylpropionic acid N-hydroxysuccinimidyl ester and
(2) antiserum to erythropoietin that has been adsorbed with human proteins that are low in erythropoietin content.

20. An antigen-antibody complex according to claim 19 wherein the human proteins are selected from the group consisting of human serum proteins that are low in erythropoietin content and human urinary proteins are low in erythropoietin content.

21. An antigen-antibody complex according to claim 20 wherein the human proteins are human serum protein.

22. An antigen-antibody complex according to claim 20 wherein the human serum proteins are substantially free of erythropoietin.

23. An antigen-antibody complex according to claim 22 wherein the human serum protein is polycythemia vera serum protein.

24. An antigen-antibody complex according to claim 23 wherein the polycythemia vera serum proteins are erythropoietin free.

25. An antigen-antibody complex according to claim 19 wherein the antiserum is selected from the group consisting of whole erythropoietin antiserum and the immunoglobulin fraction of antiserum.

26. An antigen-antibody complex according to claim 25 wherein the erythopoietin antiserum is the antierythropoietin immunoglobulin fraction.

27. An antigen-antibody complex according to claim 26 wherein the erythropoietin antiserum is the immunoglobulin fraction prepared by Rivano precipitation.

28. An antigen-antibody complex according to claim 26 wherein the erythropoietin antiserum is the IgA fraction prepared by fractionation on dextran 2-(diethylamino)ethyl 2-[[-(diethylamino)-ethyl]-diethylam(monio]ethyl ether chloride hydrochloride epichlorohydrin cross-linked.

29. An antigen-antibody complex according to claim 23 wherein an antiserum is slected from the group consisting of whole erythropoietin antiserum and the immunoglobulin fraction of antiserum.

30. An antigen-antibody complex according to claim 29 wherein the erythropoietin antiserum is the anti-erythropoietin immunoglobulin fraction.

31. An antigen-antibody complex according to claim 30 wherein the erythropoietin antiserum is the immunoglobulin fraction prepared by Rivanol precipitation.

32. An antigen-antibody complex according to claim 30 wherein the erythropoietin antiserum is the IgA fraction prepared by fractionation on dextran 2-(diethylamino)ethyl 2-[[(diethylamino)-ethyl]-diethylamino]ethyl ether chloride hydrochloride epichlorohydrin cross-linked.

33. A process for purifying a erythropoietin-conjugate having the formula

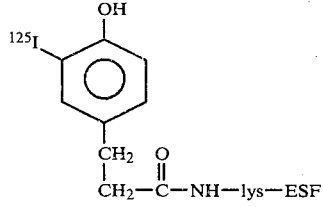

wherein ESF is erythropoietin, lys is lysine and $^{125}I$ is iodine $-125$, which comprises adsorption and dissorption of said conjugate with erythropoietin antiserum selected from the group consisting of whole erythropoietin anti-serum and the immunoglobulin fraction of erythropoietin antiserum, said antiserum having been absorbed with human proteins that are low in erythropoietin content.

34. A process according to claim 33 wherein the human serum proteins are selected from the group consisting of human serum proteins and human urinary proteins.

35. A process according to claim 34 wherein the human proteins are human serum proteins.

36. A process according to claim 35 wherein the human serum proteins are human polycythemic vera serum proteins.

37. A process according to claim 36 wherein the polycythemic vera serum protein is erythropoietin free.

38. A process according to claim 37 wherein the erythopoietin antiserum used is selected from the group consisting of whole erythropoietin antiserum and antierythropoietin immunoglobulins.

39. A process according to claim 38 wherein the erythropoietin antiserum is antierythropoietin immunoglobulins.

40. A process according to claim 39 wherein the erythropoietin antiserum is the immunoglobulin fraction prepared by Rivanol precipitation.

41. A process according to claim 39 wherein the erythropoietin antiserum is the IgA fraction prepared by fractionation on dextran 2-(diethylamino)ethyl 2-[[-(diethylamino)ethyl]-diethylammonio]ethyl ether chloride hydrochloride epichlorohydrin cross-linked.

42. A process according to claim 34 wherein the erythropoietin antiserum has been adsorbed with human urinary proteins that are low in erythropoietin content.

43. An antigen-binder complex comprising
    (a) binder-labelled erythropoietin and
    (b) binder-unlabelled erythropoietin.
wherein the binder-labelled erythropoietin has been purified by immunosorption with antiserum that has been preadsorbed with human proteins that are low in erythropoietin content.

44. An antigen-binder complex according to claim 43 wherein the labelled erythropoietin has the structure $$\text{}^{125}\text{I}-\underset{\underset{CH_2-\overset{O}{\overset{\|}{C}}-NH-lys-ESF}{|}}{\underset{CH_2}{\bigcirc}}-OH$$

wherein ESF is erythropoietin, lys is lysine and $^{125}$I is iodine -125.

45. An antigen binder complex according to claim 44 wherein the binder is anti-erythopoietin antiserum.

46. An antigen-binder complex according to claim 45 wherein the binder consists of the immunoglobulin fraction of erythropoietin antiserum.

47. A kit for the radioimmunoassay of erythropoietin comprising a container having within the container a multiplicity of smaller containers and contents said contents comprising
    (a) lyophillized assay buffer concentrate;
    (b) lyophillized rabbit anti-erythropoietin antiserum;
    (c) goat anti-rabbit gamma-globulin;
    (d) erythropoietin standards; and
    (e) erythropoietin that has been conjugated with a moniodinated succimidyl ester of 3-(4-hydroxyphenyl)-propionic acid
wherein the erythropoietin conjugate has been purified by immunosorption with antiserum that has been preadsorbed with human proteins that are low in erythropoietin content and with the proviso that each item is of such quantity that when all the items are brought together at a proper pH, dilution and temperature in the presence of an erythropoietin sample of human blood serum or plasma, antibodies in the antiserum bind to both labelled erythropoietin and erythropoietin in the sample.

48. A kit according to claim 47 wherein the human proteins are selected from the group consisting of human serum proteins and human urinary proteins.

49. A kit according to claim 48 wherein the human proteins are human serum proteins.

50. A kit according to claim 49 wherein the human serum protein is polycythemic vera sera proteins.

51. A kit according to claim 50 wherein the polycythemic vera serum proteins are erythropoietin free.

52. A kit according to claim 47 wherein a means for holding instructions for use of the smaller container contents in a radioimmunoassay for determining the level of erythropoietin in an unknown sample is within or affixed to the said container.

53. A kit according to claim 47 wherein a top wholly or partially covers the container.

* * * * *

UNITED STATES PATENT OFFICE
CERTIFICATE OF CORRECTION

Patent No. 4,254,095      Dated March 3, 1981

Inventor(s) James W. Fisher and Arvind B. Rege

It is certified that error appears in the above-identified patent and that said Letters Patent are hereby corrected as shown below:

Column 1, line 28: "special chambers of" should read: -- special chambers or --.

Column 1, line 33: "bioasay" should read: -- bioassay --.

Column 4, line 29: "iodinaed" should read: -- iodinated --.

Column 9, line 14: "dimmensions" should read: -- dimensions --.

Column 10, line 43: "proteins concentration" should read: -- protein concentration --.

Column 10, line 65: "Example 3" should read: -- Example 4 --.

Column 11, line 67: "maybe stored" should read: -- may be stored --.

Column 13, line 25: "glublin" should read: -- globulin --.

Column 14, line 19: "11.84 mu/ml." should read: -- 11.84 mu/ml (Table 5). --.

Column 16, line 54 (Claim 33): "absorbed" should read: -- adsorbed --.

Signed and Sealed this

Fourteenth Day of December 1982

[SEAL]

Attest:

GERALD J. MOSSINGHOFF

Attesting Officer     Commissioner of Patents and Trademarks